(12) United States Patent
Brandt

(10) Patent No.: US 10,618,007 B2
(45) Date of Patent: Apr. 14, 2020

(54) SYSTEMS AND METHODS OF REDUCING VIRUS MIGRATION THROUGH A VIRUS REMOVAL FILTER AFTER FEED FLOW REDUCTION

(71) Applicant: Asahi Kasei Bioprocess America, Inc., Glenview, IL (US)

(72) Inventor: Michael D. Brandt, Cassopolis, MI (US)

(73) Assignee: Asahi Kasei Bioprocess America, Inc., Glenview, IL (US)

( * ) Notice: Subject to any disclaimer, the term of this patent is extended or adjusted under 35 U.S.C. 154(b) by 65 days.

(21) Appl. No.: 15/968,445

(22) Filed: May 1, 2018

(65) Prior Publication Data

US 2019/0336915 A1 Nov. 7, 2019

(51) Int. Cl.
*B01D 61/10* (2006.01)
*B01D 61/08* (2006.01)

(52) U.S. Cl.
CPC ............. *B01D 61/10* (2013.01); *B01D 61/08* (2013.01); *B01D 2311/25* (2013.01); *B01D 2313/18* (2013.01)

(58) Field of Classification Search
CPC ...... B01F 3/04049; B01F 5/10; B08B 9/0327; C02F 1/74; C02F 2103/06; C02F 2303/02; E03B 3/12; E03B 3/18; B01D 61/10; B01D 2311/04; B01D 2311/06; B01D 2311/25; B01D 2313/18; B01D 61/08; B01D 61/14; A61L 2/0017; A61L 2/022
See application file for complete search history.

(56) References Cited

U.S. PATENT DOCUMENTS

| | | | |
|---|---|---|---|
| 4,263,253 | A | 4/1981 | Pilz et al. |
| 5,017,292 | A | 5/1991 | DiLeo et al. |
| 8,956,532 | B1 | 2/2015 | James, Jr. |
| 10,048,587 | B2 | 8/2018 | Carcasi et al. |
| 2009/0325269 | A1 | 12/2009 | Marschke |
| 2014/0262989 | A1 | 9/2014 | Pimentel et al. |

FOREIGN PATENT DOCUMENTS

| | | |
|---|---|---|
| DE | 102013113641 A1 | 6/2015 |
| EP | 0008454 A2 | 3/1980 |

OTHER PUBLICATIONS

"Process Pause in Virus Filtration", Asahi Kasei Bioprocess, (publicly available before May 1, 2018).
(Continued)

*Primary Examiner* — Dirk R Bass
(74) *Attorney, Agent, or Firm* — Marshall, Gerstein & Borun LLP

(57) ABSTRACT

A valve arrangement for reducing the migration of one or more viruses through a filter when feed flow to the filter is resumed after a reduction in the feed flow. The valve arrangement includes an inlet line having an inlet port to be connected to a supply of product and an outlet port to be connected to an inlet of the filter, a pump, an outlet line, and a recirculation system. The recirculation system includes a recirculation line connecting the outlet line and the inlet line, and a check valve disposed along the recirculation line. When the check valve detects the feed flow reduction, a recirculation loop is created such that product is continuously recirculated through the filter during the reduction, thereby ensuring continuous fluid flow through the filter even during the reduction.

23 Claims, 2 Drawing Sheets

(56) References Cited

OTHER PUBLICATIONS

Asper, Virus Breakthrough After Pressure Release During Virus Retentive Filtration, Charles River, presentation at Pharamceutical Drug Association meeting Barcelona, Spain (Jun. 27, 2011).

Chen, Laboratory Scale Studies Provide Scientific Basis for Setting Appropriate Controls in cGMP Manufacturing for Virus Filtration Unit Operation, Eli Lilly and Company, presentation at 2014 PDA/FDA Virus and TSE Safety Conference, Bethesda, Maryland (Jun. 9-11, 2014).

Dishari et al., Probing effects of pressure release on virus capture during virus filtration using confocal microscopy, Biotechnology and Bioengeering, 112(10):2115-22 (Oct. 2015).

Hongo-Hirasaki, Optimization of Virus Removal Filtration Processes: Design of Process Parameters and Virus Clearance Studies, presentation, Asahi Kasei Medical Co., Ltd. (2015).

Hongo-Hirasaki, Process Designing for Virus Removal Filtration, 17th Planova Workshop 2014, Washington, USA (Jun. 12-13, 2014).

LaCasse et al., Impact of Process Interruption on Virus Retention of Small-Virus Filters, BioProcess International, pp. 34-44 (Nov. 2013).

Strauss, Process Pause in Virus Filtration, Asahi Kasei Bioprocess, video presentation slides (Jun. 29, 2016).

Triebsch et al., Pressure Interruptions (Stop/Start) During Virus Filtration: Assuring Safety Using Robust Process Technology and an Appropriate Risk Mitigation Strategy, Application Note, 5 pp. Pall Life Sciences, (Mar. 2015).

Venkiteshwaran et al., Impact of Stop/Start of Flow During Virus Filtration on Parvovirus Cleanrance, Eli Lilly and Company, Pharmaceutical Drug Association (publicly available before May 1, 2018).

Wang, Factors Affecting the Robustness of Viral Cleanrance by 15N Filtration, Planova Workshop, Talecris Biotherapeutics (Nov. 4, 2005).

European Application No. 19171780.0, Extended European Search Report, dated Oct. 2, 2019.

SYSTEMS AND METHODS OF REDUCING VIRUS MIGRATION THROUGH A VIRUS REMOVAL FILTER AFTER FEED FLOW REDUCTION

FIELD OF THE DISCLOSURE

The present disclosure generally relates to virus filtration systems and, more particularly, to a system and method for ensuring continuous flow through a virus removal filter to prevent virus migration through the virus removal filter after a feed flow reduction.

BACKGROUND

Pharmaceutical drugs that are manufactured, extracted, or synthesized from biological sources are required to go through virus reduction steps to mitigate the potential of viral contamination in the drug product. Similarly, blood products and derivatives are required to go through virus reduction steps to mitigate the potential of viral contamination in the product. One such known method of virus reduction is through size exclusion filtering. Through size exclusion filtering, a feed flow containing the product to be filtered is passed through a virus removal filter. The virus removal filter has a virus filtration membrane that traps viruses to be removed from the product. To trap the virus, the membrane is manufactured to have millions of voids that connect to multiple capillaries that interconnect to form a lattice the fluid must pass through to exit the filter. Therefore, a virus entrained in the fluid flow has a torturous path to find a way through the virus filter membrane to exit. On this torturous path, a virus may get trapped in or about a capillary by size exclusion. It may also be held up in a void by fluid forces or affinity to the void wall. Thus, for example, to trap a virus having a 17 nanometers ("nm") cross-sectional diameter, the capillaries must have a cross section diameter of less than 17 nm somewhere along their length or a void must retain a virus having less than a 17 nanometer cross-sectional diameter by fluid forces or affinity to the walls of the void.

A reduction in feed flow through the virus removal filter may occur for various reasons during the filtration process. For example, a reduction in feed flow through the virus removal filter may occur as a result of a reduction in supply to the filter. Alternatively or additionally, a reduction in feed flow through the virus removal filter may occur as a result of valve switching, fitting failure, pneumatic failure, mechanical failure, electrical failure, and other intentional or non-intentional acts or events. In any case, as a result of such a reduction in feed flow, flow through the virus removal filter will become reduced or even discontinuous.

However, a virus which is retained by fluid flow or affinity to the walls of a void may find its way out of retention by Brownian motion when fluid flow through the void is reduced (either partially or completely). In other words, during reduced feed flow, a virus may move about a void by Brownian motion. Brownian motion may move a virus far enough away from where it was retained in the void that when full feed flow resumes through the void, a virus gets entrained in the flow and exits the void into a capillary or another void. When a virus gets entrained in the flow and exits a void after once being retained by that void, it has another chance to migrate through the virus filtration membrane, thereby undesirably increasing the chances that the virus will pass completely through the virus removal filter.

Thus, reduced or discontinuous feed flow through a virus removal filter, during the filtration process, will result in a higher probability of a virus migrating through the virus removal filter when full feed flow resumes. In other words, reduction in feed flow through a virus removal filter, during the filtration process, will increase the probability of a virus making its way through the virus removal filter when full feed flow resumes. It will therefore be appreciated that the reduction of feed flow through a virus removal filter, during the filtration process, is a concern.

BRIEF DESCRIPTION OF THE DRAWINGS

The features of this disclosure which are believed to be novel are set forth with particularity in the appended claims. The present disclosure may be best understood by reference to the following description taken in conjunction with the accompanying drawings, in which like reference numerals identify like elements in the several figures, in which:

DETAILED DESCRIPTION

The present disclosure is generally directed to a valve arrangement for reducing the migration of one or more viruses through a virus removal filter when feed flow is resumed after a feed flow reduction through the virus removal filter. The valve arrangement disclosed herein reduces the migration of one or more viruses by ensuring that continuous fluid flow is provided through the virus removal filter in the event that a reduction in feed flow through the virus removal filter occurs. In some examples, the valve arrangement recirculates fluid from the outlet of the virus removal filter to the inlet of the virus removal filter. At the same time, the valve arrangement is configured to prevent viruses in the fluid flowing to the inlet of the virus removal filter from diffusing into the outlet fluid. In some examples, once the feed flow reduction ceases and full feed flow resumes, the valve arrangement automatically supplies a recirculation buffer to help sweep out any fluid trapped in the recirculation line.

Figure 1:
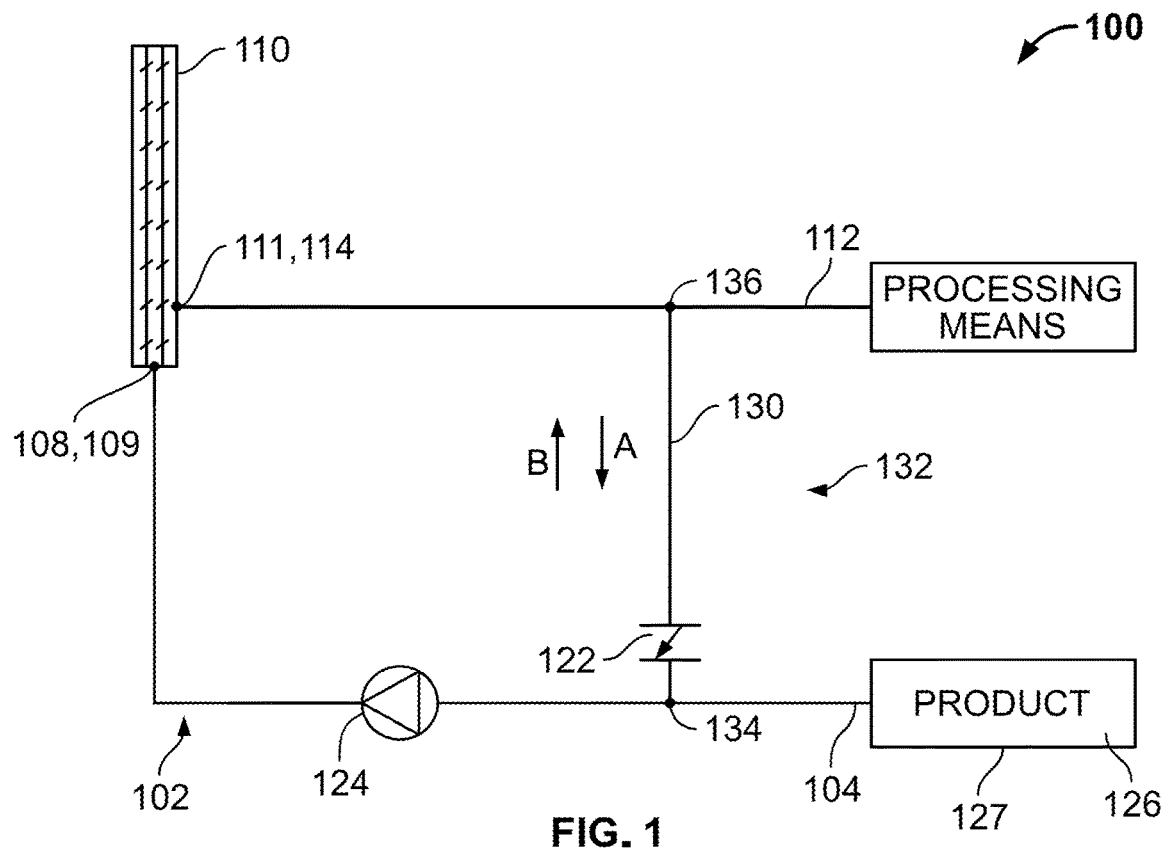
FIG. 1 is a schematic illustration of an example of a valve arrangement, constructed in accordance with the teachings of the present disclosure, for reducing the migration of one or more viruses across a virus removal membrane when full feed flow is resumed after a feed flow reduction.

FIG. 1 depicts an example of a system 100 for reducing the migration of one or more viruses across and through a virus removal filter 110 when feed flow is resumed after a feed flow reduction through the virus removal filter 110 occurs. The virus removal filter 110 has a virus filtration membrane that is generally configured to effectuate virus reduction from a product 126 (e.g., a pharmaceutical drug product in solution) flowing therethrough via size exclusion, by ensuring that fluid flow through the virus filter 110 is continuous, such that viruses are not dislodged and passed through the membrane of the virus filter 110 but are instead continuously and consistently trapped in the membrane of the virus filter 110. The virus filter 110 is preferably manufactured using regenerated cellulous, e.g., by Asahi KASEI Medical Co., LTD, though the virus filter 110 may instead be manufactured from polysulfone or polyvinylidene fluoride.

In the illustrated example, the system 100 takes the form of a valve arrangement that includes an inlet line 102 adapted to be connected to the filter 110, an outlet line 112 adapted to be connected to the filter 110, a pump 124 disposed on the inlet line 102, and a recirculation system 132 coupled to both the inlet line 102 and the outlet line 112 and configured to provide the continuous fluid flow discussed above. In other examples, however, the system 100 may include different, additional, or fewer components.

In particular, the inlet line 102 includes an inlet port 104 and an outlet port 108. The inlet port 104 is generally coupled to a supply 127 of the product 126 that is to be passed through the filter 110 for virus removal. The supply 127 of the product 126 may, for example, take the form of a tank or vessel suitable to hold the product 126. In some cases, the supply 127 may also receive or hold a buffer solution that helps pass the product 126 through the virus removal filter 110. Meanwhile, the outlet port 108 of the inlet line 102 is arranged to be connected to an inlet 109 of the filter 110. Thus, when the inlet line 102 is connected to the filter 110, the product 126 (and in some cases, the buffer solution for carrying the product 126) flows from the supply 127 and to and through the filter 110 via the inlet port 104 and the outlet port 108 of the inlet line 102. In turn, the virus filtration membrane of the filter 110 traps any viruses contained in the product 126 flowing from the supply 127.

The outlet line 112 is arranged to be coupled to an outlet 111 of the filter 110 via an inlet port 114 of the outlet line 112. When the outlet line 112 is coupled to the filter 110, the outlet line 112 exhausts the filtered product 126 (i.e., the filtrate) that has passed through the filter 110. The outlet line 112 may optionally be coupled to other devices, e.g., a processing means, to further process the product 126 or facilitate separation of the product 126 from the buffer solution (when employed).

In the illustrated example, the recirculation system 132 includes a recirculation line 130 disposed between and connecting the inlet and outlet lines 102, 112, and a check valve 122 disposed along the recirculation line 130. In particular, the recirculation line 130 includes an inlet port 134 and an outlet port 136. The inlet port 134 fluidly connects the recirculation line 130 to the inlet line 102 and the outlet port 136 fluidly connects the recirculation line 130 to the outlet line 112. The check valve 122, meanwhile, is disposed along the recirculation line 130 between the inlet port 134 and the outlet port 136, but at a position closer to, and adjacent, the inlet port 134 than the outlet port 136 (at least in this example). The check valve 122 in this example takes the form of a high-integrity, high-sensitivity backpressure regulator manufactured by, for example, Equilibar. The check valve 122 has a default, closed position in which the check valve 122 prevents fluid flow in both directions between the inlet port 134 and the outlet port 136 of the recirculation line 130, and an open position, in which the check valve 122 allows fluid flow in a direction A from the outlet port 136 to the inlet port 134 but not in a direction B from the inlet port 134 to the outlet port 136. Thus, the check valve 122 acts to ensure that no product 126 can flow to the outlet line 112 without first passing through the filter 110, regardless of its position. At the same time, the check valve 122 is also configured to detect a reduction in feed flow in the inlet line 102 (i.e., from the inlet port 104 of the inlet line 102 to the outlet port 108 of the inlet line 102, and to move between the closed and open positions depending upon whether such a reduction is detected.

During normal operation of the system 100, the check valve 122 is in its closed position and the product 126 is fed into and through the filter 110. More particularly, the pump 124 draws the product 126 from the supply 127 of the product 126 and passes the product 126 to and through the outlet port 108 of the inlet line 102 and into the filter 110. Once in the filter 110, the product 126 will pass through the virus filter membrane of the filter 110 (not shown). As discussed above, the membrane of the filter 110 has a lattice structure that consists of various interconnected voids and capillaries having diameters smaller than the cross section of the virus that is to be removed from the product 126. The diameter of the voids and capillaries of the filter membrane may be, for example, between fifteen (15) and seventy five (75) nanometers ("nm"). This lattice structure forms a tortuous path for the product 126 to flow through, which entraps the virus contained in and to be removed from the product 126. After passing through the filter membrane, the product 126 then exits the filter 110 through the filter outlet 111 and enters the outline line 112 via an inlet port 114. Once within the outlet line 112, the product 126 may be exhausted from the system 100.

During the course of normal operation, a reduction in feed flow through the inlet line 102 may occur. In particular, the feed flow from the inlet port 104 to the outlet port 108 of the inlet line 102 may be reduced (and in some cases, totally interrupted). The reduction may occur for a variety of reasons. For example, the buffer solution used to help pass the product 126 through the filter 110 may be depleted prior to the entirety of the product 126 being filtered through the filter 110, the inlet port 104 may become obstructed, preventing flow through the inlet line 102, or a person may inadvertently step on a portion of the inlet line 102, causing an obstruction. In any case, in the event that such a reduction occurs, the present disclosure provides ways of reducing virus migration through by resumption of the feed flow following the reduction in feed flow.

When feed flow is reduced through the inlet line 102 (and, thus, the filter 110), the system 100 responds in a manner that reduces virus migration through the virus removal filter 110. As discussed above, the check valve 122 is arranged to detect a reduction in feed flow through the inlet line 102. When the check valve 122 detects a feed flow reduction (e.g., by virtue of the pump 124 pulling on the check valve 122), the check valve 122 moves from its closed position to its open position. This, in turn, allows fluid to flow in the direction A from the outlet port 136 to the inlet port 134, thereby creating a recirculation loop in the system 100, i.e., from the inlet line 102 through the filter 110, the filter 110 to the outlet line 112, the outline line 112 to the recirculation line 130, and the recirculation line 130 back to the inlet line 102. The creation of this recirculation loop allows the pump 124 to continuously recirculate product 126 through the outlet port 108 of the inlet line 102 and the filter 110, such that fluid continuously flows to and through the filter 110 during the feed flow reduction, and thereby mitigates virus mobility by ensuring that a virus trapped in the filter membrane of the filter 110 remains immobilized during the feed flow reduction. In some cases, e.g., when feed flow is fully interrupted through the inlet line 102, the pump 124 will continuously recirculate substantially all of the product 126 that is in or has passed through the inlet line 102 and not yet been exhausted out of the system via the outlet line 112. In other cases, e.g., when feed flow is only partially reduced, the pump 124 will recirculate at least a portion of the product

126 that is in or has passed through the inlet 102, with that portion being equal to the amount of feed flow reduction. As an example, when there is a feed flow reduction of 50%, the pump 124 will recirculate approximately 50% of the product 126 that is in or has passed through the inlet 102, while the remaining approximately 50% will be exhausted out of the system 100, such that the total fluid flowing through the inlet 102 is approximately equal to the amount flowing therethrough prior to the reduction.

The system 100 will continue to recirculate fluid in this manner until such time that the reduction ceases and full feed flow resumes. Once the check valve 122 detects that full feed flow has resumed, the check valve 122 moves from its open position to its closed position, such that fluid can no longer flow from the outlet line 112 to the inlet line 102 via the recirculation line 130, and thereby closing the recirculation loop.

Figure 2:
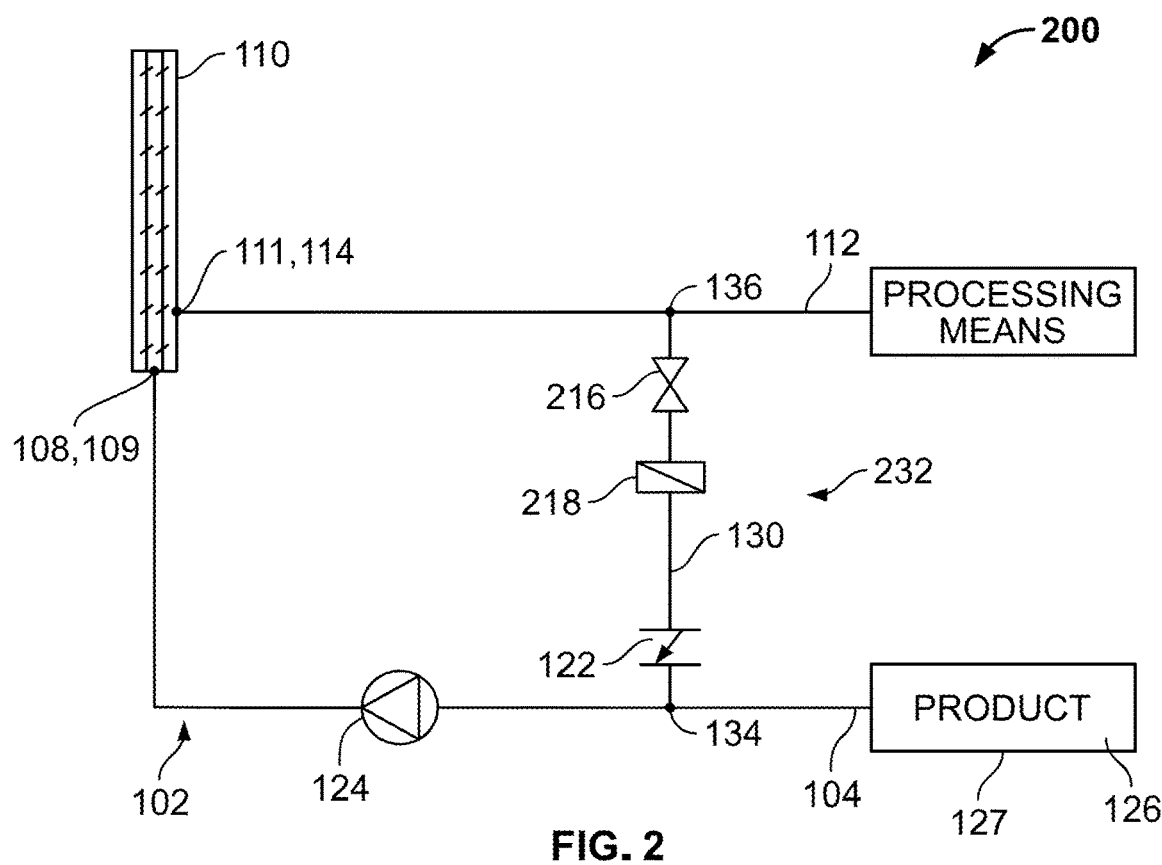
FIG. 2 is a schematic illustration of another example of a valve arrangement, constructed in accordance with the teachings of the present disclosure, for reducing the migration of one or more viruses across a virus removal membrane when full feed flow is resumed after a feed flow reduction.

FIG. 2 depicts an example of a system 200 for reducing the migration of one or more viruses across and through the virus removal filter 110 when full feed flow is resumed after a feed flow reduction occurs. The system 200 depicted in FIG. 2 is similar to the system 100 illustrated in FIG. 1, with common components depicted using common reference numerals, but is different in that the system 200 includes a recirculation system 232 that is different from the recirculation system 132 of the system 100. In this example, the recirculation system 232 includes the check valve 122, but also includes a shut-off valve 216 and a rupture disc 218 each disposed on the recirculation line 130.

The shut-off valve 216 is disposed along the recirculation line 130 between the inlet port 134 and the outlet port 136, but at a position closer to, and adjacent, the outlet port 136 (at least in this example). The shut-off valve 216 has an open position, in which the valve 216 allows fluid flow between the inlet port 134 and the outlet port 136, and a closed position, in which the valve 116 prevents fluid flow between the inlet port 134 and the outlet port 136. In other words, when the shut-off valve 216 is in the closed position, the shut-off valve 216 redundantly prevents any fluid flow from the inlet port 134 of the recirculation line 130 to the outlet port 136 of the recirculation line 130, in the event that the check valve 122 fails or the product 126 somehow flows through the check valve 122. Meanwhile, the rupture disc 218 is also disposed along the recirculation line 130 between the inlet port 134 and the outlet port 136, but at a position between the check valve 122 and the shut-off valve 216. The rupture disc 218 has a membrane that seals off the recirculation line 130 but fails at a pre-determined differential pressure, at which time fluid can flow therethrough unobstructed.

During normal operation of the system 200, the check valve 122 is closed, the shut-off valve 216 is open (though it may instead be closed), and the product 126 flows through the inlet line 102, through the filter 110, and out of the system 200 via the outlet line 112 in a similar manner as described above in connection with the system 100. Further, because the check valve 122 is closed, a uniform pressure differential (or a substantially uniform pressure differential) exists across the rupture disc 218, such that the forces on both sides of the rupture disc 218 are equal. This uniform pressure differential across the rupture disc 218 ensures that the rupture disc 218 remains intact and seals off the recirculation line 130.

However, when a feed flow reduction occurs in the inlet line 102 (and, thus, the filter 110) during normal operation of the system 200, the system 200 responds in a manner that reduces the potential for virus migration through the virus removal filter 110. When the check valve 122 detects a feed flow reduction, the check valve 122 moves from its closed position to its open position and the shut-off valve 216 is moved from its closed position to its open position (if it was closed) responsive to, for example, instructions from the check valve 122 to do so or instructions from a controller (not shown). This, in turn, allows the pump 124 to exert a negative pressure on the rupture disc 218, i.e., exposes the rupture disc 218 to a non-uniform pressure differential. The non-uniform pressure differential creates a force on one side of the rupture disc 218 that is greater than the force exerted on the other side of the rupture disc 218. This uneven distribution of forces causes the rupture disc 218 to burst (i.e., permanently open).

When the rupture disc 218 bursts, and so long as the check valve 122 and the shut-off valve 216 are in their open positions, it will be appreciated that fluid will have an unobstructed path to flow from the outlet port 136 to the inlet port 134, which allows fluid to flow from the outlet line 112 to the inlet line 102 through the recirculation line 130. This creates a recirculation loop in the system 200, i.e., from the inlet line 102 through the filter 110, the filter 110 to the outlet line 112, the outlet line 112 to the recirculation line 130, and the recirculation line 130 back to the inlet line 102. The creation of this recirculation loop allows the pump 124 to continuously recirculate product 126 through the outlet port 108 of the inlet line 102 and the filter 110 during the feed flow reduction, such that fluid continuously flows to and through the filter 110 during the feed flow reduction, and thereby mitigates virus mobility by ensuring that a virus trapped in the filter membrane of the filter 110 remains immobilized during the feed flow reduction. In some cases, e.g., when feed flow is fully interrupted, the pump 124 will continuously recirculate substantially all of the product 126 that is in or has passed through the inlet line 102 and not yet been exhausted out of the system via the outlet line 112. In other cases, e.g., when feed flow is only partially reduced, the pump 124 will recirculate at least a portion of the product 126 that is in or has passed through the inlet 102, with that portion being equal to the amount of fluid reduction. As an example, when there is a feed flow reduction of 50%, the pump 124 will recirculate approximately 50% of the product 126 that is in or has passed through the inlet 102, while the remaining approximately 50% will be exhausted out of the system 100, such that the total fluid flowing through the inlet 102 is approximately equal to the amount flowing therethrough prior to the reduction.

The system 200 will continue to recirculate the product 126 until such time that the reduction ceases and full feed flow resumes. Once the check valve 122 detects that full feed flow has resumed, the check valve 122 moves from its open position to its closed position, and the system 200 causes the shut-off valve 216 to transition from its open position to its closed position, such that fluid can no longer flow from the outlet line 112 to the inlet line 102 via the recirculation line 130, thereby closing the recirculation loop. In other words, the outlet line 112 is fluidly isolated from the inlet line 102.

Of course, once the shut-off valve 216 has returned to closed position and there is no longer an reduction in feed flow, the rupture disc 218 within the recirculation system 232 will have to be replaced. For example, a person may be required to manually removed the used rupture disc 218 and put an new rupture disc 218 in its place. In another example, however, the replacement of the rupture disc 218 may be automated. Automation of the replacement acts as a redundancy incase a person forgets to replace the disc and helps to create a more autonomous system 200.

Figure 3:
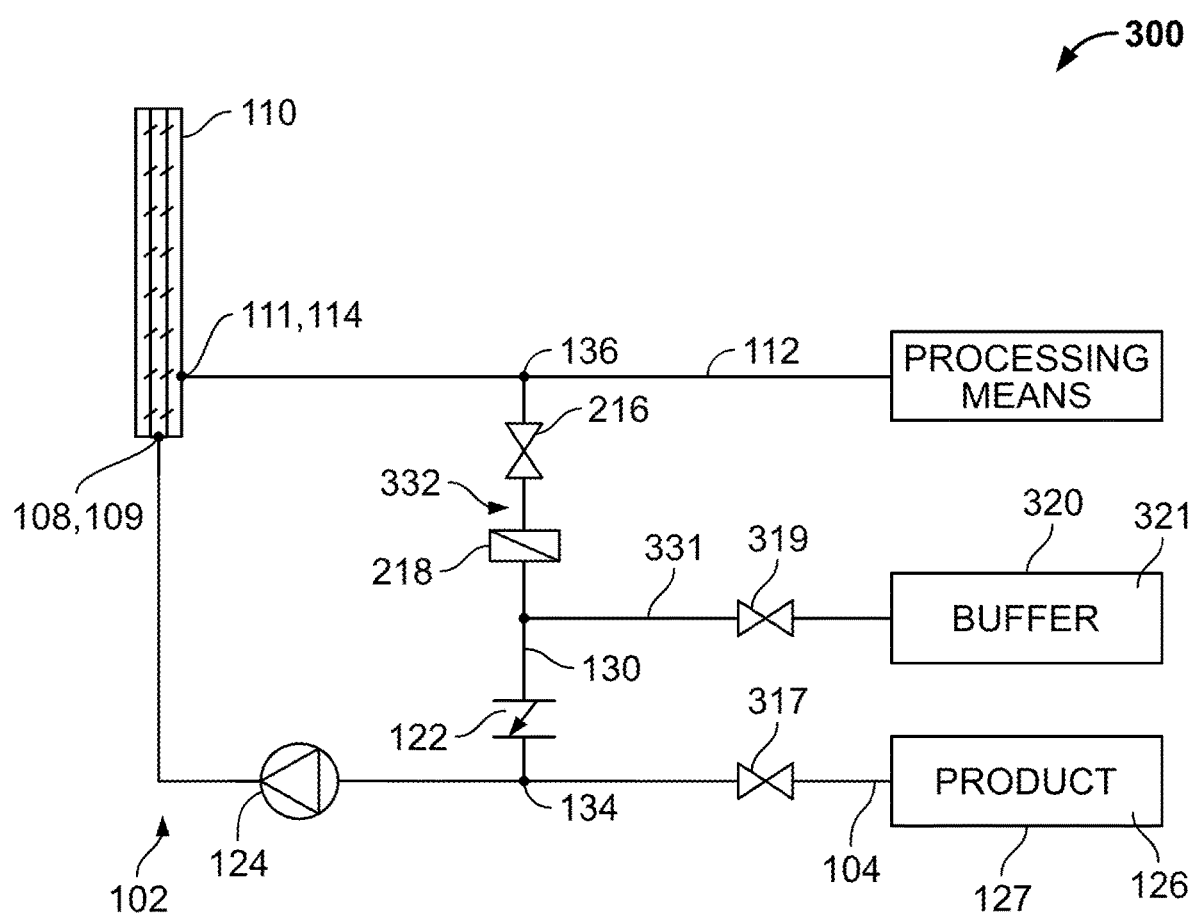
FIG. 3 is a schematic illustration of another example of a valve arrangement, constructed in accordance with the teachings of the present disclosure, for reducing the migration of one or more viruses across a virus removal membrane when full feed flow is resumed after a feed flow reduction.

FIG. 3 depicts an example of a system 300 for reducing the migration of one or more viruses across and through the virus removal filter 110 when feed flow is resumed after a feed flow reduction through the virus removal filter 110 occurs. The system 300 depicted in FIG. 3 is similar to the system 200 illustrated in FIG. 2, with common components depicted using common reference numerals, but is different in that the system 300 includes a recirculation system 332 that is different from the recirculation system 232 of the system 200. In particular, the recirculation system 332 in this example includes the check valve 122, the shut-off valve 216, and the rupture disc 218, but also includes a second shut-off valve 317, a third shut-off valve 319, and a source 320 of recirculation buffer solution 321 (i.e., second buffer solution).

As illustrated in FIG. 3, the second shut-off valve 317 is disposed along the inlet line 102 at a position between the pump 124 and the inlet port 104. More particularly, the second shut-off valve 317 is disposed along the inlet line 102 between the inlet port 134 of the recirculation line 130 and the inlet port. Like the shut-off valve 216, the second shut-off valve 317 has an open position and a closed position. But when the shut-off valve 317 is in its open position, the valve 317 allows fluid flow between the inlet port 104 and the inlet port 134. Thus, when the shut-off valve 317 is in its open position, the valve 317 allows product 126 to flow from the source 127 to the pump 124. Conversely, when the shut-off valve 317 is in its closed position, the valve 317 prevents fluid flow between the inlet port 104 and the inlet port 134, such that no product 126 can flow to the pump 124 (i.e., the feed flow is zero).

The third shut-off valve 319 and the source 320 of recirculation buffer solution 321 are fluidly connected to the recirculation line 130. In the illustrated example, the third shut-off valve 319 and the source 320 are each disposed along a recirculation branch line 331 that is connected to the recirculation line 130 between the check valve 122 and the rupture disc 218. When the recirculation branch line 331 so connected to the recirculation line 130, the third shut-off valve 319 is disposed between the recirculation line 130 and the source 320 of recirculation buffer solution 321. Like the shut-off valve 317, the third shut-off valve 319 has an open position and a closed position. But when the shut-off valve 319 is in its open position, the valve 319 allows fluid flow between the source 320 and the recirculation line 130. Thus, when the shut-off valve 319 is in its open position, the valve 319 allows the recirculation buffer solution 321 to flow from the source 320 to the recirculation line 130. Conversely, when the shut-off valve 319 is in its closed position, the valve 319 prevents fluid flow between the source 320 and the recirculation line 130.

The system 300 operates in a similar manner as the system 200 during normal operation and responsive to a feed flow reduction in the inlet line 102 (and, thus, the filter 110). In particular, during normal operation of the system 300, the check valve 122 is closed, the first shut-off valve 216 is open (though it may alternatively be closed), the second shut-off valve 317 is open, and the third shut-off valve 319 is closed, such that the product 126 flows through the inlet line 102, through the filter 110, and out of the system 200 via the outlet line 112. And when the check valve 122 detects a feed flow reduction in the inlet line 102, the check valve 122 moves from its closed position to its open position and the first shut-off valve 216 is moved from its closed position to its open position (if it was closed), thereby creating a recirculation loop in the system 300, just as described above in connection with the system 200.

However, once the feed flow reduction ceases and full feed flow resumes, the system 300 is configured to automatically (i.e., without human intervention) sweep any fluid trapped in the recirculation line 130 from the recirculation line 130 and out of the system 300. More particularly, once the check valve 122 detects that full feed flow has resumed, the check valve 122 moves from its open position to its closed position, and the system 200 causes the first shut-off valve 216 to transition from its open position to its closed position, the second shut-off valve 317 to move from its open position to its closed position, and the third shut-off valve 319 to move from its closed position to its open position. Thus, while the inlet line 102 is fluidly isolated from the outlet line 112, the recirculation buffer solution 321 flows from the source 320 to and through the third shut-off valve 319, via the recirculation branch line 331, and to and through the check valve 122, via the recirculation line 130. In doing so, the recirculation buffer solution 321 sweeps any fluid that would otherwise be trapped within the recirculation line 130 when the check valve 122 detects that full feed flow has resumed. This trapped fluid subsequently flows through the inlet line 102, to and through the virus removal filter 110, and is exhausted out of the system 300 via the outline line 112.

It will be appreciated that the components of the system 100, the system 200, and the system 300 may be made from one or more different materials. Preferably, the components of the system 100, the system 200, and the system 300, e.g., the inlet line 102, the outlet line 112, and the recirculation line 130, each take the form of a conduit made from a disposable material, such as a plastic material like gamma stable plastic (which can withstand gamma radiation). However, in some examples, the inlet line 102, the outlet line 112, the recirculation line 130, and/or other components may instead be made from a metal material (e.g., stainless steel).

Those skilled in the art will recognize that a wide variety of modifications, alterations, and combinations can be made with respect to the above described embodiments without departing from the scope of the disclosure, and that such modifications, alterations, and combinations are to be viewed as being within the ambit of the inventive concept.

The invention claimed is:

1. A valve arrangement for reducing the migration of one or more viruses through a virus removal filter when feed flow to the virus removal filter is resumed following a reduction in the feed flow, the valve arrangement comprising:
    an inlet line having an inlet port and an outlet port, the inlet port connected to a supply of a product to be passed through a virus removal filter that filters viruses from the product, and the outlet port connected to an inlet of the virus removal filter;
    a pump disposed on the inlet line between the inlet port and the outlet port to feed the product to the inlet of the filter;
    an outlet line having an inlet port connected to an outlet of the filter to exhaust the filtered product from the filter;
    a recirculation system arranged to continuously recirculate fluid through the valve arrangement when feed flow is reduced from the inlet port of the inlet line to the outlet port of the inlet line, the recirculation system comprising:

a recirculation line having an inlet port connected to the inlet line and an outlet port connected to the outlet line; and a check valve disposed along the recirculation line between the inlet port of the recirculation line and the outlet port of the recirculation line, the check valve configured to detect that the feed flow has been reduced;

wherein, when the feed flow has been reduced, the pump causes the check valve to move from a closed position, in which the check valve prevents fluid flow between the inlet and outlet ports of the recirculation line, to an open position, in which the check valve allows fluid flow from the outlet port of the recirculation line to the inlet port of the recirculation line, thereby creating a recirculation loop comprising the inlet line through the filter, the filter to the outlet line, the outlet line to the recirculation line, and the recirculation line to the inlet line, such that product is continuously recirculated through the filter during the feed flow reduction.

2. The valve arrangement of claim 1, wherein when the feed flow reduction has ceased, the pump causes the check valve to move from the open position to the closed position, thereby closing the recirculation loop.

3. The valve arrangement of claim 1, wherein the recirculation system further comprises a first shut-off valve disposed along the recirculation line, the shut-off valve having an open position, in which the first shut-off valve allows fluid flow between the inlet and outlet ports of the recirculation line, and a closed position, in which the first shut-off valve prevents fluid flow between the inlet and outlet ports of the recirculation line.

4. The valve arrangement of claim 3, wherein when the feed flow has been reduced, the first shut-off valve moves from the closed position to the open position.

5. The valve arrangement of claim 3, wherein the recirculation system further comprises a rupture disc disposed along the recirculation line between the outlet port of the recirculation line and the first shut-off valve, and wherein when the first shut-off valve is in the open position and the check valve is in the open position, the pump causes the rupture disc to burst.

6. The valve arrangement of claim 5, wherein the recirculation system further comprises a supply of recirculation buffer solution fluidly connected to the recirculation line between the check valve and the first shut-off valve.

7. The valve arrangement of claim 6, wherein the recirculation system further comprises a second shut-off valve disposed along the inlet line between the pump and the supply of the product to selectively fluidly connect the supply of the product with the pump.

8. The valve arrangement of claim 7, wherein the recirculation system further comprises a third shut-off valve disposed between the check valve and the supply of recirculation buffer solution to selectively fluidly connect the supply of recirculation buffer solution to the recirculation line.

9. The valve arrangement of claim 1, wherein the inlet line, the outlet line, the pump, the recirculation line, and the check valve are each made from a disposable material.

10. The valve arrangement of claim 9, wherein the disposable material comprises a gamma stable plastic material.

11. A valve arrangement for reducing the migration of one or more viruses through a virus removal filter when feed flow to the virus removal filter is resumed following a reduction in the feed flow, the valve arrangement comprising:

an inlet line having an inlet port and an outlet port, the inlet port connected to a supply of a product to be passed through a virus removal filter that filters viruses from the product, and the outlet port connected to an inlet of the virus removal filter;

a pump disposed on the inlet line between the inlet port and the outlet port to feed the product to the inlet of the filter;

an outlet line having an inlet port connected to an outlet of the filter to exhaust the filtered product from the filter;

a recirculation system arranged to continuously recirculate fluid through the valve arrangement when feed flow is reduced from the inlet port of the inlet line to the outlet port of the inlet line, the recirculation system comprising:

a recirculation line having an inlet port connected to the inlet line and an outlet port connected to the outlet line; and a check valve disposed along the recirculation line between the inlet port of the recirculation line and the outlet port of the recirculation line, the check valve configured to detect that the feed flow has been reduced;

wherein, when the feed flow has been reduced, the pump causes the check valve to move from a closed position, in which the check valve prevents fluid flow between the inlet and outlet ports of the recirculation line, to an open position, in which the check valve allows fluid flow from the outlet port of the recirculation line to the inlet port of the recirculation line, thereby creating a recirculation loop comprising the inlet line through the filter, the filter to the outlet line, the outlet line to the recirculation line, and the recirculation line to the inlet line, such that product is continuously recirculated through the filter during the feed flow reduction, wherein when the feed flow reduction has ceased, the pump causes the check valve to move from the open position to the closed position, thereby closing the recirculation loop, and wherein the inlet line, the outlet line, the pump, the recirculation line, and the check valve are each made from a disposable material.

12. The valve arrangement of claim 11, wherein the recirculation system further comprises a first shut-off valve disposed along the recirculation line, the shut-off valve having an open position, in which the first shut-off valve allows fluid flow between the inlet and outlet ports of the recirculation line, and a closed position, in which the first shut-off valve prevents fluid flow between the inlet and outlet ports of the recirculation line.

13. The valve arrangement of claim 12, wherein when the feed flow has been reduced, the first shut-off valve moves from the closed position to the open position.

14. The valve arrangement of claim 12, wherein the recirculation system further comprises a rupture disc disposed along the recirculation line between the outlet port of the recirculation line and the first shut-off valve, and wherein when the first shut-off valve is in the open position and the check valve is in the open position, the pump causes the rupture disc to burst.

15. The valve arrangement of claim 14, wherein the recirculation system further comprises a supply of recirculation buffer solution fluidly connected to the recirculation line between the check valve and the first shut-off valve.

16. The valve arrangement of claim 15, wherein the recirculation system further comprises:

a second shut-off valve disposed along the inlet line between the pump and the supply of the product to selectively fluidly connect the supply of the product with the pump; and a third shut-off valve disposed between the check valve and the supply of recirculation buffer solution to selectively fluidly connect the supply of recirculation buffer solution to the recirculation line.

17. A method for reducing the migration of one or more viruses through a virus removal filter when feed flow to the virus removal filter is resumed following a reduction in the feed flow, the method comprising:

providing an inlet line having an inlet port and an outlet port;

providing an outlet line having an inlet port;

connecting the inlet port to a supply of a product to be passed through the virus removal filter, connecting the outlet port to an inlet of a virus removal filter that filters viruses from the product, and connecting the inlet port of the outlet line to an outlet of the filter to exhaust the filtered product from the filter;

providing a recirculation system comprising a recirculation line and a check valve disposed along the recirculation line, the recirculation line having an inlet port and an outlet port;

connecting the inlet port of the recirculation line to the inlet line and the outlet port of the recirculation line to the outlet line;

facilitating feed flow of the product from the supply of the product to the outlet port of the inlet line via a pump disposed on the inlet line between the inlet port and the outlet port of the inlet line; and responsive to detecting a reduction in the feed flow, creating a recirculation loop formed by the inlet line through the filter, the filter to the outlet line, the outlet line to the recirculation line, and the recirculation line to the inlet line, such that product is continuously recirculated through the filter during the feed flow reduction.

18. The method of claim 17, wherein creating the recirculation loop comprises moving the check valve from a closed position, in which the check valve prevents fluid flow between the inlet and outlet ports of the recirculation line, to an open position in which the check valve allows fluid flow from the outlet port of the recirculation line to the inlet port of the recirculation line.

19. The method of claim 17, wherein providing the recirculation system further comprises providing a first shut-off valve disposed along the recirculation line, the shut-off valve having an open position, in which the first shut-off valve allows fluid flow between the inlet and outlet ports of the recirculation line, and a closed position, in which the first shut-off valve prevents fluid flow between the inlet and outlet ports of the recirculation line.

20. The method of claim 19, wherein responsive to detecting the reduction, moving the first shut-off valve from the closed position to the open position.

21. The method of claim 19, wherein providing the recirculation system further comprises providing a rupture disc disposed along the recirculation line between the outlet port of the recirculation line and the first shut-off valve.

22. The method of claim 19, wherein providing the recirculation system further comprises providing a supply of recirculation buffer solution fluidly connected to the recirculation line between the check valve and the first shut-off valve.

23. The method of claim 19, wherein providing the recirculation system further comprises:

providing a second shut-off valve disposed along the inlet line between the pump and the supply of the product to selectively fluidly connect the supply of the product with the pump; and providing a third shut-off valve disposed between the check valve and the supply of recirculation buffer solution to selectively fluidly connect the supply of recirculation buffer solution to the recirculation line.

* * * * *